United States Patent [19]
Roberg et al.

[11] Patent Number: 5,599,964
[45] Date of Patent: Feb. 4, 1997

[54] CONTINUOUS PROCESS FOR PREPARING HYDROCARBYLALUMINOXANES

[75] Inventors: John K. Roberg; Robert E. Farritor; Edward A. Burt, all of Baton Rouge, La.

[73] Assignee: Albemarle Corporation, Richmond, Va.

[21] Appl. No.: 635,310

[22] Filed: Apr. 19, 1996

[51] Int. Cl.$^6$ .................................................. C07F 5/06
[52] U.S. Cl. ................................................... 556/179
[58] Field of Search ............................................. 556/179

[56] References Cited

U.S. PATENT DOCUMENTS

| | | | |
|---|---|---|---|
| 3,219,591 | 11/1965 | Vandenberg | 252/431 |
| 3,242,099 | 3/1966 | Manyik | 252/429 |
| 3,300,458 | 1/1967 | Manyik | 260/88.2 |
| 4,730,071 | 3/1988 | Schoenthal et al. | 556/179 |
| 4,730,072 | 3/1988 | Schoenthal et al. | 556/179 |
| 4,772,736 | 9/1988 | Edwards et al. | 556/179 |
| 4,908,463 | 3/1990 | Bottelberghe | 556/179 |
| 4,924,018 | 5/1990 | Bottelberghe | 556/179 |
| 4,937,363 | 6/1990 | Smith, Jr. et al. | 556/179 |
| 4,960,878 | 10/1990 | Crapo et al. | 556/179 |
| 4,968,827 | 11/1990 | Davis | 556/179 |
| 5,041,584 | 8/1991 | Crapo et al. | 556/179 |
| 5,041,585 | 8/1991 | Deavenport et al. | 556/179 |
| 5,086,024 | 2/1992 | Crapo et al. | 502/117 |
| 5,206,401 | 4/1993 | Deavenport et al. | 556/175 |
| 5,403,942 | 4/1995 | Becker et al. | 556/175 |
| 5,427,992 | 6/1995 | Graefe et al. | 502/111 |

OTHER PUBLICATIONS

Manyik et al., A Soluble Chromium–Based Catalyst for Ethylene Trimerization and Polymerization, Journal of Catalysis, vol. 47, 1977, pp. 197–209.

*Primary Examiner*—Paul F. Shaver
*Attorney, Agent, or Firm*—Philip M. Pippenger

[57] ABSTRACT

Aluminoxane is made by feeding water, hydrocarbylaluminum and organic solvent to a loop recycle reactor under conditions so as to react the water and hydrocarbylaluminum to form a hydrocarbylaluminoxane, removing a portion of the solvent and hydrocarbylaluminoxane from said reactor and recirculating the remaining portion of the reactor contents through a reaction zone where the water initially contacts the hydrocarbylaluminum. The feed rates of water, hydrocarbylaluminum and solvent to the reactor and the withdrawal rate of solvent and hydrocarbylaluminoxane from the reactor can be adjusted to produce a substantially steady state reaction.

20 Claims, 3 Drawing Sheets

CONTINUOUS PROCESS FOR PREPARING HYDROCARBYLALUMINOXANES

This invention relates generally to the production of aluminoxanes by reacting water with hydrocarbylaluminum compounds and more specifically to an improved continuous process for making hydrocarbylaluminoxanes, and especially oligomeric methylaluminoxanes, using a loop recycle reactor.

Vandenberg, U.S. Pat. No. 3,219,591 reported the catalytic activity of compounds formed by the reaction of trialkylaluminum with limited amounts of water in the polymerization of epichlorohydrin and other oxiranes. Shortly thereafter, Manyik, et al. U.S. Pat. No. 3,242,099 reported the use of aluminoxanes, made by reacting 0.85–1.05 moles of water with hydrocarbylaluminum compounds such as triisobutylaluminum, as co-catalysts with certain transition metal compounds in the polymerization of mono-unsaturated alpha-olefins; e.g. ethylene and propylene. Isobutylaluminoxane was also made by adding an equal mole quantity of water to a heptane solution of triisobutylaluminum.

Manyik, et al. U.S. Pat. No. 3,300,458 prepare alkylaluminoxane by passing a hydrocarbon through water to form a wet hydrocarbon and mixing the wet hydrocarbon and an alkyl aluminum/hydrocarbon solution in a conduit.

Schoenthal, et al. U.S. Pat. No. 4,730,071 show the preparation of methylaluminoxane by dispersing water in toluene using an ultrasonic bath to cause the dispersion and then adding a toluene solution of trimethylaluminum to the dispersion. Schoenthal, et al. U.S. Pat. No. 4,730,072 is similar except it uses a high speed, high shear-inducing impeller to form the water dispersion.

Edwards, et al. U.S. Pat. No. 4,772,736 describe an aluminoxane preparation process in which water is introduced below the surface of a solution of hydrocarbylaluminum adjacent to a stirrer which serves to immediately disperse the water in the hydrocarbon solution.

Bottelberghe U.S. Pat. No. 4,908,463 describe an aluminoxane preparation process in which a static mixer is used to disperse water in a solvents and then impinges the water dispersion with a hydrocarbylaluminum solution in a T-shaped reactor. The solution is then removed to a finished reaction vessel which is stirred and can have a cooling means such as a heat-exchanger in an external pump-around loop.

Becker et al U.S. Pat. No. 5,403,942 and Graefe et al. U.S. Pat. No. 5,427,992 describe batch processes for preparing aluminoxanes by injecting water into trialkylaluminum solutions using respectively, a jet loop reactor and a rotor/stator machine to mix the water and trialkylaluminum.

A problem associated with free water addition to trialkylaluminum to produce aluminoxane solutions in organic solvents is that the solutions may produce gel and/or small particles which aggregate to form gel on standing. Even when the particles and/or gel are removed by filtration, additional gel can form in the solution after 2 or 3 weeks, especially when originally-prepared dilute solutions are concentrated to contain higher aluminoxane contents which are convenient for storage, shipment and use.

Another problem is the nonuniformity of the products which contain a variable and wide range of molecular weights which as believed to be a cause of inconsistency in catalyst activity when the aluminoxanes are used in polymerization reactions. These problems are more pronounced when producing methylaluminoxanes which are preferred for use in metallocene catalyzed olefin polymerization and copolymerization processes. Trimethylaluminum is extremely reactive with water which makes a uniform reaction difficult to achieve.

A continuous process has now been found which economically produces aluminoxanes having improved stability and uniformity.

In accordance with this invention there is provided a continuous process for making aluminoxane, said process comprising feeding water, hydrocarbylaluminum and organic solvent to a loop recycle reactor under conditions so as to react said water and said hydrocarbylaluminum to form a hydrocarbylaluminoxane, removing a portion of said solvent and hydrocarbylaluminoxane from said reactor and recirculating the remaining portion of the reactor contents through a reaction zone where said water initially contacts said hydrocarbylaluminum. The feed rates of water, hydrocarbylaluminum and solvent to said reactor and the withdrawal rate of solvent and hydrocarbylaluminoxane from said reactor can be adjusted so as to produce a substantially steady state reaction.

Figure 1:
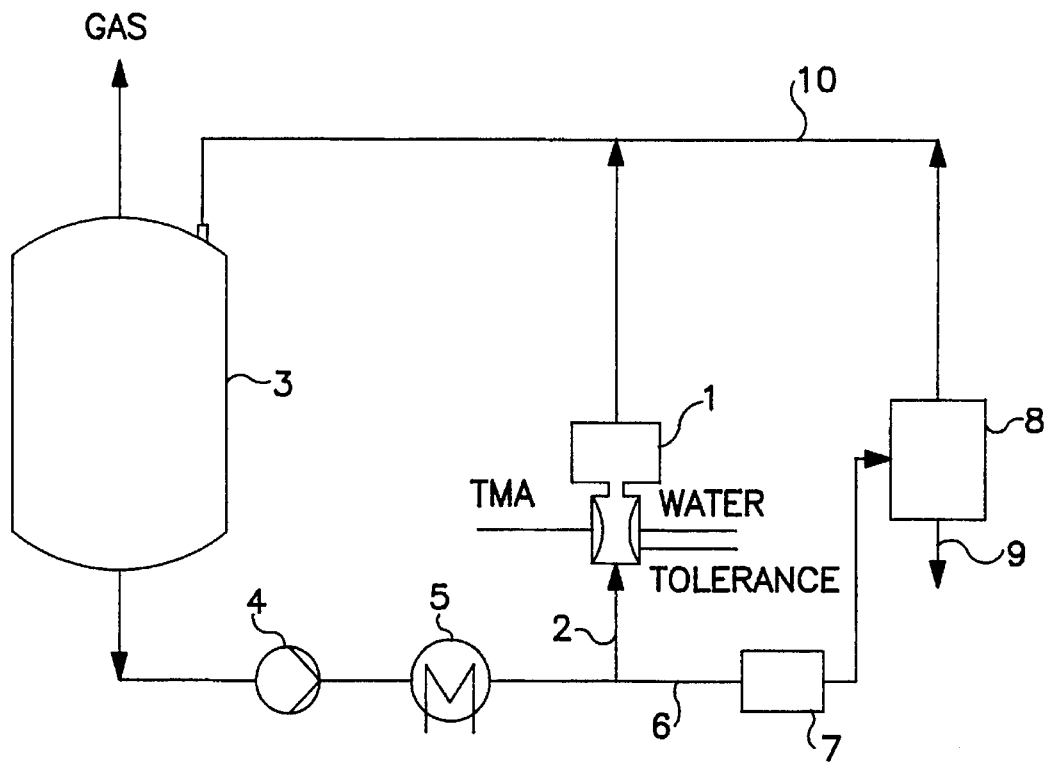
FIG. 1 is a schematic diagram showing a pumparound reactor system which injects water, hydrocarbylaluminum and solvent into an in-line mixing device according to one embodiment of the process of the invention.

Hydrocarbylaluminoxanes may exist in the form of linear, cyclic, caged or polymeric structures with the simplest compounds being a tetraalkylaluminoxane such as tetramethylaluminoxane, $(CH_3)_2AlOAl(CH_3)_2$, or tetraethylaluminoxane, $(C_2H_5)_2AlOAl$—$(C_2H_5)_2$. The compounds preferred for use in olefin polymerization catalysts are oligomers, sometimes referred to as polyethylaluminoxanes, and usually contain about 4 to 20 of the repeating units:

where R is $C_1$–$C_8$ alkyl and is preferably methyl. The exact structure of aluminoxanes has not been defined and they may contain linear, cyclic, caged and/or cross-linked species. Methylaluminoxanes (MAOs) normally have lower solubility in organic solvents than higher alkylaluminoxanes and the methylaluminoxane solutions tend to be cloudy or gelatinous due to the separation of particles and agglomerates. In order to improve the solubility of the methylaluminoxane, higher alkyl groups, e.g. $C_2$ to $C_{20}$ can be included such as by hydrolyzing a mixture of trimethylaluminum with up to 50 mole percent of a $C_2$ to $C_{20}$ alkylaluminum compound such as, for example, triethylaluminum, tri-n-propylaluminum, triisobutylaluminum, tri-n-hexylaluminum, tri- n-octylaluminum or a triarylaluminum. The MAO's can also contain up to about 20 mole percent, based on aluminum, of moieties derived from amines, alcohols, ethers, esters, phosphoric and carboxylic acids, thiols, alkyl and aryl disiloxanes and the like to further improve activity, stability and/or solubility. Such modified and mixed methyl-higher alkyl or aryl aluminoxanes are included in the term "methylaluminoxane" as used herein.

Any hydrocarbyl aluminum compound or mixture of compounds capable of reacting with water to form an aluminoxane can be used. This includes, for example, trialkylaluminum, triarylaluminum, mixed alkyl arylaluminum, alkylaluminum hydride and the like.

The preferred hydrocarbyl aluminum compounds are the alkylaluminum compounds, especially trialkylaluminum compounds such as trimethylaluminum, triethylaluminum, triisobutylaluminum, tri-n-hexylaluminum, trioctylaluminum and the like. Of these, the more preferred are the tri-$C_{1-4}$-alkylaluminum compounds.

The reaction is carried out in an inert solvent. Any inert solvent can be used. The preferred solvents are aliphatic and aromatic hydrocarbons. Aromatic hydrocarbons are more preferred such as toluene, xylene, ethylbenzene, cumene, mesitylene and the like. The most preferred solvent is toluene.

The water can be added to the reaction either neat and/or dissolved or dispersed in the solvent. The reactants are combined in proportions to provide from about 0.5 to 8.0 moles of hydrocarbyl aluminum compound per mole of water. When making methylaluminoxanes, the proportions are preferably from about 1.3 to 6.0 moles of trimethylaluminum and more preferably from about 2.0 to 4.0 moles per mole of water.

The reaction temperature ranges from about −70° to 100° C. with a preferred range of about −50° to 50° C. and a more preferred range of from about −20° to 20° C.

In the embodiment of the process of the invention which is illustrated in FIG. 1, water, trimethylaluminum (TMA) and toluene are continuously injected into the inlet of an inline mixer 1 which is located in a reactor pumparound loop 2. Besides introducing TMA at the mixer, all or part of it can be fed to the reactor at other points, such as between pump 4 and cooler 5. The water and TMA react and the reaction mixture, which includes product methylaluminum (MAO) and unreacted TMA, are circulated through loop 2 to degassing tank 3 where methane gas is vented. The reaction mixture is then pumped back to the inlet of in-line mixer 1 such as an IKA Works in-line disperser, whose rotor operates at speeds of from about 7,000 to 13,000 rpm, by pump 4. The heat of reaction is maintained within a selected temperature range by use of cooler 5. MAO product in solvent, which contains unreacted TMA, is continuously drawn off through line 6, passed to a setting or filtration device 7 and then to flash unit 8. Concentrated MAO in toluene is drawn off at the bottom of flash unit 8 through line 9. The TMA and solvent which are flashed from the product can be returned to degasser 3 through line 10. Except when fresh TMA is added to the system as neat TMA, some solvent is separated from the flashed aluminum alkyl/solvent in order to preserve the material balance. The TMA and solvent can also be fed to line 2 ahead of the in-line mixer if desired. The in-line mixer produces a homogeneous reaction zone and the large volume recycle of product stream provides both heat absorption and dilution of the reactants, especially the water, such that localized overheating and/or any significant temperature rise is avoided. The continuous introduction of reactant and withdrawal of product permits a constant concentration of reactants to be maintained in a steady state reaction which helps to achieve a more uniform and reproducible product in improved yields. It also permits the sequential production of a variety of products simply by adjustment of the reactant feed rates and ratios.

Figure 2:
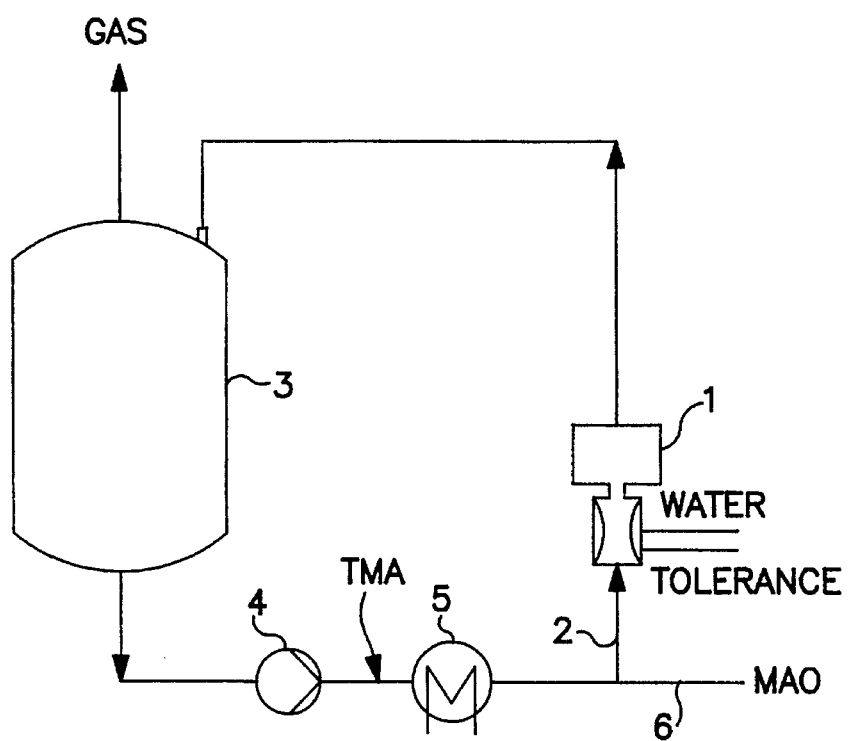
FIG. 2 is a schematic diagram showing a pumparound reactor system used in the embodiment of the process of the invention described in Example 1.

FIG. 2 shows a system which does not include product processing and TMA and solvent recycle. Also, the TMA is fed to the system between the pump and cooler rather than at the mixer.

Figure 3:
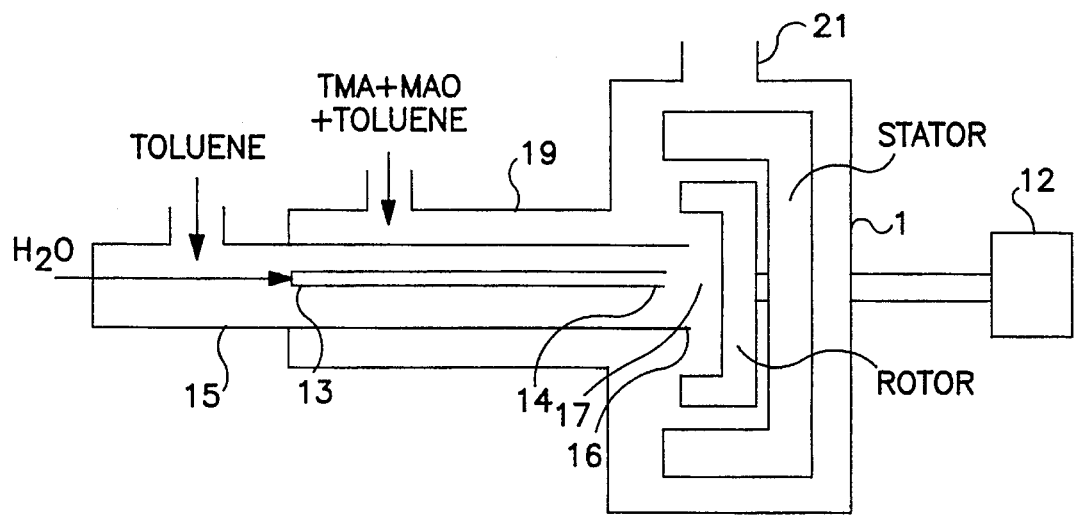
FIG. 3 is a schematic cross-sectional view of a water and solvent injector and in-line mixing system used in the embodiment of the process of the invention described in Example 1.

FIG. 3 illustrates a device suitable for introducing water and solvent to a reaction zone in a reactor/stator in-line mixer 1 driven by motor 12. Water passes through a capillary tube 13 which is coaxially arranged within tube 15 which has a diameter of, for example, 3.0 mm. The tip 14 of capillary tube 13 is recessed about 1 to 2 mm from the end 16 of tube 15. Solvent passing through tube 15 sweeps water from tip 14 into the reaction zone 17 where the water reacts with a TMA-MAO-solvent mixture which enters reaction zone 17 through tube 19. The reaction mixture exits from rotor/stator in-line mixer 1 through outlet 21. The inner diameter of capillary tube 13 can be selected to deliver either a stream or individual droplets of water. For example, inner diameters of from 0.001 to 0.1 mm. The end of the water injection tube or nozzle should be positioned so that the water does not contact and collect on the wall of the solvent conduit. In general, the ratio of the weight of the flow of solvent used to carry the water to the reaction zone to the weight of water ranges from about 10 to 1 to 1000 to 1 and preferably from about 25 to 1 to 150 to 1. Other suitable methods and devices can be used to introduce water to the reaction. For example, the water could be predispersed in solvent and the water/solvent dispersion fed to the reaction zone through a single conduit. The shape of the tubes or conduits is not critical and they can have other than a circular cross-section. Also, other mixing devices can be used which provide high shear in the reaction zone including, but not limited to, ultrasonic, propeller and static mixers. In fact, it was found that a good product in high yield could be obtained even when the rotor/stator mixer was turned off (0 rpm). The hydrocarbylaluminum compounds and aluminoxane products are protected from oxygen and moisture by means of an inert gas atmosphere, such as dry nitrogen.

The volumes and flow rates of the water, solvent and recycle stream provide a very dilute concentration of water to give a more uniform hydrolysis reaction. For example, the total stream is at least 200 times the volume of water feed, preferably 5,000 times greater, and more preferably at least 8,000 times greater. The water is entirely soluble in the higher flow of solvent and plugging of the reactor, which can occur when using a continuous T-type reactor due to localized over reaction, is avoided. The result is a stable reaction without need of interruption to clear blockages. The high pumparound flow minimizes any temperature rise due to the highly exothermic hydrolysis reaction. Relative concentrations of water and hydrocarbylaluminum compound in the reaction zone can be maintained substantially constant by continually adding makeup hydrocarbyl aluminum and water in the proportions that they are reacted and removed from the pumparound flow and it is thereby possible to achieve a steady state reaction.

The reaction feed and product removal rates are preferable adjusted to give a concentration of crude aluminoxane product in solvent of from about 1 to 5 weight percent. The concentration of unreacted hydrocarbylaluminum can range from 0 to 10 weight percent. When making MAO, the MAO product concentration generally ranges from about 20 to 30 weight percent and unreacted TMA from about 2 to 10 based on the total weight of MAO, TMA and solvent. Feed rates depend upon the size of the reactor used. The crude aluminuoxane product can be concentrated by removal of solvent and unreacted alkyl aluminum compound.

The process of the invention is further illustrated by, but is not intended to be limited to, the following examples.

EXAMPLE 1

Example 1 used an apparatus similar to the one illustrated in FIGS. 2 and 3 where fresh TMA in toluene solution was introduced into the system between pump 4 and cooler 5 and water was injected into the system at the inlet of in-line mixer 1.

The feeds were 11.8 weight percent trimethylaluminum (TMA) in toluene under nitrogen pressure, toluene (10 ppm water) under nitrogen pressure and deionized water purged with helium. The TMA solution and water were fed by metering pumps and the toluene was fed on nitrogen pressure. The in-line mixer 1 was a IKA-Works UTL 25 with a dispersion chamber and "fine" dispersing elements. The degasser 3 was a glass cylinder vessel with stainless steel heads having about a 10 liter volume. The system used a centrifugal pump 4 and a pumparound cooler 3 with water-ethylene glycol coolant. To begin operation, the degasser 3 was charged with toluene (3.18 kg, 34.5 g mol, 3.65 liters, the pumparound cooler was started and the bulk temperature was brought down to 8° C. The flow through the mixer was 727 kg/hr, 7890 g mol/hr. of toluene. The mixer was started and set to run at 7000 rpm (t=0). The toluene feed was started (ave. 2.0 kg/hr, 21.7 gmol/hr) five minutes later (t=5 min). At t=10 minutes the TMA feed was started (ave. 5.5 kg/hr; 0.65 kg/hr TMA+4.85 kg/hr toluene, 9.0 gmol/hr TMA, 52.7 gmol/hr toluene). At t=20 minutes the water feed was started (0.8 g/min, 2.67 gmol/hr $H_2O$). Crude MAO product was continuously withdrawn to maintain a constant level in the system. The reaction conditions in mixer 1 were; temperature 9°–11° C., $H_2O$/TMA molar feed ratio 0.30, bulk/$H_2O$ flow volume ratio about 17,000, bulk/$H_2O$ mass flow ratio about 15,000. The expected Al weight percent was 3.25 weight percent and the residence time constant was 25 minutes. At least three time constants are needed to turn over 99% of the vessel contents.

A series of samples were pulled to look at steady state and the results are shown in Table 1.

TABLE 1

| Sample | Time (+) Min | Time Constant | % Al | TMA Wt. % | % Vol Solids | Al as TMA |
|---|---|---|---|---|---|---|
| 1 | 110 | 3.6 | 3.19 | 5.10 | 3 | 60% |
| 2 | 169 | 6.0 | 3.43 | 5.42 | 5 | 59% |
| 3 | 227 | 8.3 | 3.56 | 5.60 | 5 | 59% |

Collection of crude MAO was begun at t=108 minutes, 3.5 time constants and ended at t=236 minutes, 8.6 time constants. A total mass of 15.9 kg was collected. Filtration and analysis of a portion of crude MAO indicated that the amount of aluminum lost to solids was about 2%, i.e. the aluminum yield of the crude MAO process was 98%. Analysis 3.39 weight percent Al, 5.36 weight percent TMA, 59% Al as TMA.

EXAMPLE 2

Figure 4:
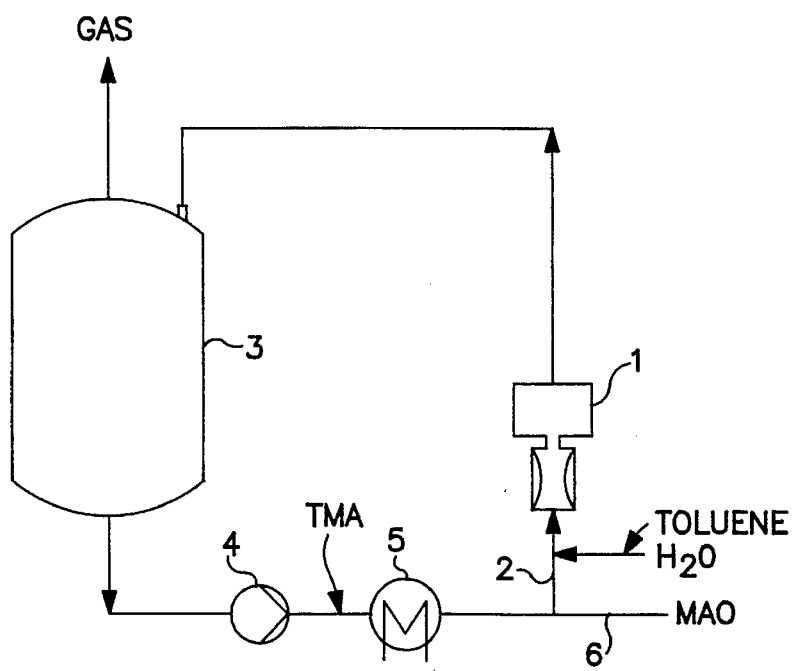
FIG. 4 is a schematic diagram showing a pumparound reactor system used in the embodiment of the process of the invention described in Example 2.
Figure 5:
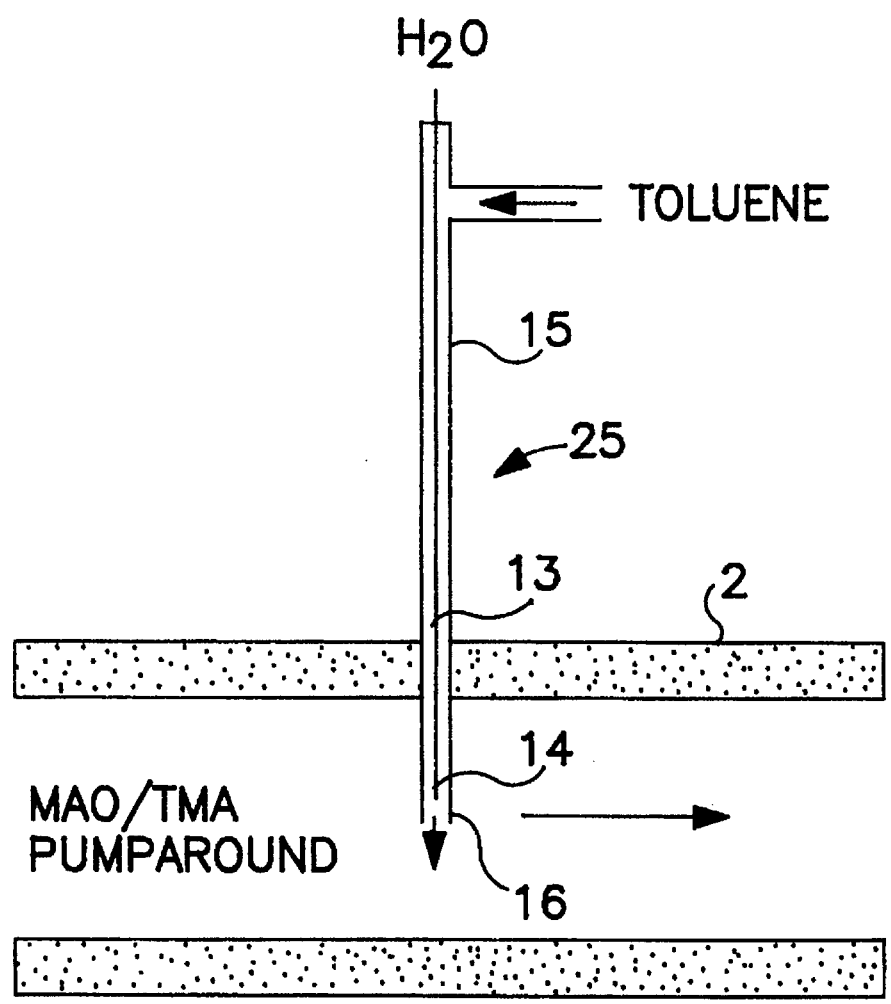
FIG. 5 is a schematic diagram showing a water injection system used in carrying out the embodiment of the process of the invention described in Examples 2 and 3.

The apparatus used is shown in FIGS. 4 and 5. The water was injected into the pumparound loop ahead of mixer 1 rather than at the inlet. Injector system 25 as illustrated in FIG. 5 has the solvent tube 15 and water capillary tube 13 arranged about perpendicular to the flow of solvent, product MAO and unreacted TMA in pumparound loop 2. Tip 14 of tube 13 is recessed about 1 mm from the end 16 of tube 15. The inner diameter of water capillary tube 13 is 0.55 mm and its outer diameter is 0.65 mm. The inner diameter of solvent tube 15 is 1.4 mm and its outer diameter is 3.2 mm. The inner diameter of loop 2 is 9.4 mm and its outer diameter is 12.7 mm. The remainder of the system shown in FIG. 4 is the same as the system used in Example 1 (FIG. 2). The feeds were 12.3 weight percent TMA in toluene under nitrogen pressure, toluene (10 ppm water) under nitrogen pressure and deuterated water (purged with helium). The TMA solution and water were fed by metering pumps and the nitrogen was fed under nitrogen pressure. The degasser was charged with 3.65 (4.09 L) of TMA solution and the bulk temperature was brought down to 2°–3° C. The flow through the mixer was 522 kg/hr and the mixer was started and set to run at 7500 rpm (t=0). The toluene feed was started at t=40 minutes (ave. 1.5 kg/hr, 16.3 gmol/hr); the TMA feed at t=48 minutes (ave. 6.0 kg/hr: 0.74 kg/hr TMA+5.26 kg/hr toluene, 10.2 gmol/hr TMA, 57.2 gmol/hr toluene); and the water feed at t=140 min (0.4 g min, 1.33 gmol/hr $H_2O$). The reaction zone temperature was 2°–3° C., the $H_2O$/TMA mole feed ratio was 0.13, the bulk/$H_2O$ flow volume ratio was about 24,000 and the bulk/$H_2O$ mass flow ratio was about 22,000. The expected Al weight percent was 3.7 weight percent and the residence time constant was 29 minutes. Crude MAO was continuously withdrawn to maintain a constant level in the system and collected at t=323 minutes, 6.3 time constants. After t=248 minutes, the mixer was turned off and two samples were analyzed to look at steady state. The results are shown in Table 2.

TABLE 2

| Sample | Time (+) Min | Time Constant | % Al | TMA Wt. % | % Vol Solids | Al as TMA |
|---|---|---|---|---|---|---|
| 1[a] | 248 | 3.7 | 3.53 | 7.95 | 0 | 84% |
| 2[b] | 423 | 9.8 | 3.68 | 8.28 | 0 | 84% |

[a] sampled just after the mixer was turned off
[b] mixer off

Collection of crude MAO was completed at t=423 minutes, 9.8 time constants with a total mass of 13.6 kg collected. No visible solids were immediately observed in the crude MAO sample. After about 1 week of storage at −15° C., a very faint film of solids appeared at the bottom of the sample bottles. Aluminum yield is estimated to be greater than 99%. Analysis: 3.68 weight percent Al, 8.28 weight percent TMA, 84 percent Al as TMA.

EXAMPLE 3

The apparatus used is shown in FIGS. 4 and 5 except that part of the pumparound flow was sent through a second cooler arranged in parallel with cooler 5 and re-entered loop 2 after the crude MAO product removal point. The rotor of mixer 1 was not turned on (rpm=0). The feed materials were the same as for Example 2 except that deionized water was used. The degasset was charged with 6.4 kg, 7.2 L of TMA solution (12.3%) and the bulk temperature was brought down to 1°–3° C. The flow through mixer 1 was 545 kg/hr. The TMA feed was started (t=0) (ave 8.2 kg/hr: 1.0 kg/hr TMA+7.2 kg/hr toluene, 14.0 gmol/hr TMA, 78 gmol/hr toluene) and then at t=6 minutes the toluene feed was started (ave. 1.2 kg/hr, 12.8 gmol/hr. The water feed was started at t=21 minutes (0.89 g/min, 3.0 gmol/hr $H_2O$). The reaction zone temperature was 1°–3° C, the $H_2O$ TMA molar feed ratio was 0.21, the bulk/$H_2O$ flow volume ratio was about 11,000 and the bulk/hr mass flow ratio was about 10,000. The expected Al weight percent was 3.99 weight percent and the residence time constant was 41 minutes. The crude MAO was continuously withdrawn to maintain a constant level and at t=213 minutes, 4.7 time constants collection was begun and ended at 273 minutes, 6.1 time constants with 10.9 kg collected. Analysis of a sample taken at t=270 minutes gave 3.93 wt percent Al, 7.5 weight percent TMA, 72% Al as TMA. No visible solids were immediately observed in the crude MAO samples. After about one week of storage at −15° C. a very faint film of solids appeared at the bottom of the sample bottles. Aluminum yield was estimated to be greater than 99%.

Comparison

Crude MAO was prepared using a system similar to that used for Example 1 but run as a batch rather than a continuous process. There was no addition of any TMA during the process or continuous withdrawal of crude MAO. The feed materials were the same as for Example 3. The degasser was charged with 3.1 kg, 4.0 L, 5.25 g mol of 12.3% TMA in toluene and the bulk temperature brought down to 6°–10° C. The flow through mixer 1 was 682 kg/hour, 766 L/hr. The mixer was started (t=0) and set to run at 7400 rpm. The toluene feed was started at t=25 minutes (ave 2.0 kg/hr, 21.7 gmol/hr) and the water feed (0.4–0.8 g/min 1.33–2.67 gmol/hr) 5 minutes later (t=30 min). The total water fed at t=150 minutes was 67 g, 3.72 gmol. The temperature in the reaction zone was 6°–10° C. the overall $H_2O$/TMA molar ratio was 0.71, the bulk/$H_2O$ flow volume>16,000 and the bulk/$H_2O$ mass flow ratio>14,000. A mass of 1.3 kg of crude MAO was collected for further processing. Filtration and analysis of the crude MAO indicated that the amount of aluminum lost to solids was about 17%, such that the crude batch MAO process had an aluminum yield of only about 83%.

What is claimed is:

1. A continuous process for making aluminoxane, said process comprising feeding water, hydrocarbylaluminum and organic solvent to a loop recycle reactor under conditions so as to react said water and said hydrocarbylaluminum to form a hydrocarbylaluminoxane, removing a portion of said solvent and hydrocarbylaluminoxane from said reactor and recirculating the remaining portion of the reactor contents through a reaction zone where said water initially contacts said hydrocarbylaluminum.

2. The process of claim 1 wherein the feed rates of water, hydrocarbylaluminum and solvent to said reactor and the withdrawal rate of solvent and hydrocarbylaluminoxane from said reactor produce a substantially steady state reaction.

3. The process of claim 1 wherein said hydrocarbylaluminum is a trialkylaluminum and from about 0.5 to 8.0 moles of water per mole of trialkylaluminum are fed to the reactor.

4. The process of claim 3 wherein said trialkylaluminum is trimethylaluminum and from about 1.3 to 6.0 moles of water per mole of trimethylaluminum are fed to the reactor.

5. The process of claim 1 wherein the reaction temperature is from about −70° to 100° C.

6. The process of claim 1 wherein the solvent and hydrocarbylaluminumoxane portion which is removed from the reactor contains unreacted hydrocarbylaluminum and hydrocarbylaluminum and solvent are separated from said portion and returned to said reactor.

7. The process of claim 1 wherein said water is fed to said reaction zone in an organic solvent.

8. The process of claim 1 wherein said water is fed to said reactor through a conduit whose outlet is enclosed in a flow of organic solvent such that said solvent carries said water from the outlet of said conduit into said reactor.

9. The process of claim 1 wherein said reaction zone includes a liquid mixing means.

10. The process of claim 9 wherein said mixing means is a static mixer.

11. The process of claim 9 wherein said mixing means is an ultrasonic mixer.

12. The process of claim 9 wherein said mixing means is a rotor/stator mixer.

13. The process of claim 9 wherein said mixing device is a high shear mixer.

14. The process of claim 1 wherein a solution of hydrocarbylaluminum in solvent is fed to said reactor.

15. The process of claim 1 wherein neat hydrocarbylaluminum is fed to said reactor.

16. The process of claim 3 wherein said trialkylaluminum contains a mixture of methyl groups and one or more higher alkyl groups.

17. The process of claim 16 wherein the trialkylaluminum contains at least 50 mole percent methyl groups.

18. The process of claim 1 wherein the total volume of the liquid stream passing through said reaction zone is at least 200 times the volume of water.

19. The process of claim 18 wherein the total volume of the liquid stream passing through said reaction zone at least 5000 times the volume of water.

20. The process of claim 1 wherein said hydrocarbylaluminoxane is a methylaluminoxane.

* * * * *